(12) United States Patent
Splinter

(10) Patent No.: US 8,059,274 B2
(45) Date of Patent: Nov. 15, 2011

(54) LOW-LOSS POLARIZED LIGHT DIVERSION

(75) Inventor: Robert Splinter, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 321 days.

(21) Appl. No.: 11/952,223

(22) Filed: Dec. 7, 2007

(65) Prior Publication Data

US 2009/0147257 A1  Jun. 11, 2009

(51) Int. Cl.
*G01J 4/00* (2006.01)
(52) U.S. Cl. ......... 356/364; 600/431; 600/476; 600/478
(58) Field of Classification Search .................. 356/364, 356/477, 497, 479; 600/431, 476, 478
See application file for complete search history.

(56) References Cited

U.S. PATENT DOCUMENTS

| | | | |
|---|---|---|---|
| 5,321,774 A * | 6/1994 | Barnard et al. ................. 385/16 |
| 5,434,669 A * | 7/1995 | Tabata et al. .................. 356/477 |
| 6,438,396 B1 | 8/2002 | Cook et al. | |
| 6,527,708 B1 * | 3/2003 | Nakamura et al. ........... 600/160 |
| 2002/0196446 A1 | 12/2002 | Roth et al. | |
| 2003/0028100 A1 | 2/2003 | Tearney et al. | |
| 2003/0058440 A1 * | 3/2003 | Scott et al. .................... 356/318 |
| 2006/0241495 A1 | 10/2006 | Kurtz | |
| 2007/0109553 A1 | 5/2007 | Feldchtein et al. | |
| 2007/0165234 A1 | 7/2007 | Podoleanu | |
| 2007/0177152 A1 | 8/2007 | Tearney et al. | |
| 2007/0179487 A1 | 8/2007 | Tearney et al. | |
| 2007/0290145 A1 * | 12/2007 | Viellerobe et al. ......... 250/459.1 |
| 2008/0308730 A1 * | 12/2008 | Vizi et al. ...................... 250/309 |
| 2009/0040426 A1 * | 2/2009 | Mather et al. ................... 349/65 |

OTHER PUBLICATIONS

De Boer, Johannes F. et al., "Determination of the Depth-Resolved Stokes Parameters of Light Backscattered From Turbid Media by Use of Polarization-Sensitive Optical Coherence Tomography," Optics Letters, vol. 24, No. 5, pp. 300-302, Mar. 1, 1999.
De Boer, Johannes F. et al., "Two-Dimensional Birefringence Imaging in Biological Tissue by Polarization-Sensitive Optical Coherence Tomography," Optics Letters, vol. 22, No. 12, pp. 934-936, Jun. 15, 1997.
Everett, M. J. et al., "Birefringence Characterization of Biological Tissue by Use of Optical Coherence Tomography," Optics Letters, vol. 23, No. 3, pp. 228-230, Feb. 1, 1998.

(Continued)

*Primary Examiner* — Tarifur Chowdhury
*Assistant Examiner* — Isiaka Akanbi
(74) *Attorney, Agent, or Firm* — Sheridan Ross P.C.; Scott J. Hawranek

(57) ABSTRACT

An optical sensor that provides lateral viewing while maintaining light polarization is disclosed according to one embodiment of the invention. The sensor includes a sensor body, at least one waveguide and at least one refractive optical element. The sensor body may includes proximal end and a distal end. The waveguide includes a proximal end coincident near the proximal end of the sensor body and a distal end coincident at a point near the distal end of the sensor body. The waveguide may include one or more fiber optic. The waveguide may be positioned within the sensor body. The refractive optical element may be positioned within the sensor near the distal end of the waveguide and may be configured to refract light received from the distal end of the waveguide outward from the sensor. The refractive optical element may include one or more prisms.

26 Claims, 6 Drawing Sheets

OTHER PUBLICATIONS

Finlay, HM et al., "Fabric Organization of the Subendothelium of the Human Brain Artery by Polarized-Light Microscopy," Arteriosclerosis and Thrombosis, vol. 11, No. 3, pp. 681-690, May/Jun. 1991.

He, Michael R. et al., "Polarization-Sensitive Low-Coherence Reflectometer for Birefringence Characterization and Ranging," J. Opt. Soc. Am. B., vol. 9, No. 6, pp. 903-908, Jun. 1992.

Kemp, Nate J. et al., "Fibre Orientation Contrast for Depth-Resolved Identification of Structural Interfaces in Birefringent Tissue," Phys. Med. Biol., vol. 51, pp. 3759-3767, 2006.

McMurray, Tom et al., "Thermal Damage Quantification From Tissue Birefringence Image Analysis," SPIE, vol. 1905, pp. 140-151, Aug. 1993.

Nadkarni, Seemantini K. et al., "Measurement of Collagen and Smooth Muscle Cell Content in Atherosclerotic Plaques Using Polarization-Sensitive Optical Coherence Tomography," Journal of the American College of Cardiology, vol. 49, No. 13, pp. 1474-1481, Apr. 3, 2007.

Pierce, Mark C. et al., "Advances in Optical Coherence Tomography Imaging for Dermatology," The Journal of Investigative Dermatology, vol. 123, No. 3, pp. 458-463, Sep. 2004.

Saxer, Christopher E. et al., "High-Speed Fiber-Based Polarization-Sensitive Optical Coherence Tomography of in Vivo Human Skin," Optics Letters, vol. 25, No. 18, pp. 1355-1357, Sep. 15, 2000.

Schoenenberger, Klaus et al., "Mapping of Birefringence and Thermal Damage in Tissue by Use of Polarization-Sensitive Optical Coherence Tomography," Applied Optics, vol. 37, No. 25, pp. 6026-6036, Sep. 1, 1998.

\* cited by examiner

LOW-LOSS POLARIZED LIGHT DIVERSION

BACKGROUND

This disclosure relates in general to polarization sensitive sensors and, but not by way of limitation, to lateral viewing and polarization maintaining sensing devices amongst other things.

Tissue birefringence can be used as a diagnostic tool for tissue state, such as damage, and tissue identification. Tissue birefringence is the result of protein structure anisotropy, such as found in collagen, configured in a highly organized cellular matrix. The birefringence is the result of geometrical organization of the local index of refraction of the various tissue structures and tissue components. This inhomogeneity in refractive index provides spatial gradients in refractive index (n), as a result the light propagation in either forward (transmissions) or backward (backscattered) direction reveals spatial variations in intensity.

Prior studies in biological samples have found the effects of dichroism to be minimal in skin and muscle tissue, and have focused on measurement of retardation due to birefringence for contrasting different types of tissue and assessing the severity of burns. Tissue birefringence can be determined by probing tissue with light of known polarization state and measuring the changes in the polarization state after the light propagates through the tissue.

Optical coherence tomography (OCT) is a technique for in-vivo microscopy which obtains micron-scale cross-sectional images of subsurface structure in biological tissues. While conventional OCT measures the depth-resolved reflectivity profile of backscattered light, polarization-sensitive OCT (PS-OCT) systems have been developed to add the capability of controlling the polarization state of light incident upon the sample and measuring the reflectivity of light returning in particular polarization states. Such selectivity allows for the measurement of birefringence and/or dichroism. PS-OCT systems avoid the polarization artifacts that often occur in conventional OCT images of birefringent samples.

Most conventional OCT systems use non-polarization-maintaining (PM) single-mode fiber interconnections because they are inexpensive, allow for easy alignment and handling, and enable flexible sample arm designs which are important for in vivo measurements such as surgical and endoscopic applications.

PS-OCT systems use light of known polarization to image a target. In many applications, the target is located within vessel or small cavity and may be located on the wall of the target. As such, probes or sensors with forward sensing or forwarding probing may not accurately image the vessel or cavity wall. These challenges are also found in industrial applications as well as various medical applications.

BRIEF SUMMARY

Embodiments of the present invention provide for an optical sensor that provides lateral viewing while maintaining light polarization. This sensor may be used in various industrial and medical applications, such as PS-OCT catheter applications and non destructive testing applications. The sensor provides lateral viewing with minimal polarization loss. Such a sensor may be used in RF ablation, laser catheter ablation, catheters, stent placement, endoscopic applications, as well as industrial non-destructive testing applications.

An optical sensor that provides lateral viewing while maintaining light polarization is disclosed according to one embodiment. The sensor includes a sensor body, at least one optical waveguide and at least one refractive optical element. The sensor body may include a proximal end and a distal end. The waveguide may include a proximal end coincident near the proximal end of the sensor body and a distal end coincident at a point near the distal end of the sensor body. The waveguide may include one or more fiber optics. The waveguide may be positioned within the sensor body. The refractive optical element may also be positioned within the sensor body near the distal end of the waveguide and may be configured to refract light received from the distal end of the waveguide outward from the sensor body. The refractive optical element may include one or more prisms, such as, multi angular prisms.

The sensor may comprise a catheter or an endoscope. The refractive optical element may refract light at an angle of about 40° to about 90° measured from the outer surface of the sensor body. The sensor may also include a lumen within the sensor body. The sensor body may include an aperture configured to allow light refracted from the refractive optical element to pass through the sensor body toward a target and configured to allow light reflected from the target to pass through the sensor body toward the refractive optical element.

The refractive optical element may include two prisms. The first prism may be configured to receive light from the waveguide and refract the light at an angle of about 20° to about 45° measured from the outer surface of the sensor body. The second prism may be configured to receive light from the first prism and refract the light at an angle of about 20° to about 45° measured from the outer surface of the sensor body. The two prisms may be coupled as a single element. The waveguide may be a single mode fiber optic.

The sensor may also include a beam splitter coupled with the proximal end of the waveguide, one ore more light sources coupled with the beam splitter, and a detector coupled with the beam splitter. The light source may produce light that is propagated through the beam splitter and the waveguide, and may be refracted by the refractive optical element toward a target. The refractive optical element may refract light reflected and/or scattered from the target through the refractive optical element through the waveguide and toward the detector through the beam splitter. The light source may provide cross polarized light and/or elliptically polarized light. A polarizer may also be included.

A method for using an optical sensor that provides lateral viewing while maintaining light polarization is provided according to another embodiment. The method includes inserting the sensor into a target of interest and conducting light from a light source through a waveguide within the sensor toward the distal end of the sensor. Light may then be refracted toward the target using a refractive optical element from within the sensor. Light may exit the refractive optical element laterally from the longitudinal direction of the sensor. The refracted light may be scattered from the target back toward the refractive optical element within the sensor and conducted toward the proximal end of the sensor through the waveguide. The light may be refracted an angle greater 50° and less than or equal to 90° from the longitudinal direction of the sensor.

The method may further include receiving the light scattered from the target at a light detector and providing an image of the target using PS-OCT algorithms from the light received at the detector. The method may also include detecting light at a light detector. This detecting may include detecting the light in more than one polarization state. The refractive optical element may include one or more prisms.

A catheter that provides lateral viewing while maintaining light polarization is provided according to another embodiment. The catheter includes a catheter body, a light source, at least one fiber optic, and at least one refractive optical element. The light source may be configured to provide cross-polarized light and/or elliptically polarized light and may be coupled with the catheter body. The fiber optic may include a distal end and proximal end. The proximal end of the fiber optic is coincident near the proximal end of the catheter body and the distal end of the fiber optic is coincident at a point near the distal end of the catheter body. The fiber optic may be positioned within the catheter body. Moreover, the fiber optic may be configured to receive light from the light source at the proximate end of the fiber optic and may be configured to guide the light to the distal end of the fiber optic. The refractive optical element may be positioned within the catheter near the distal end of the fiber optic. The refractive optical element may be configured to refract light received from the distal end of the fiber optic outward from the catheter.

An optical sensor that provides lateral viewing while maintaining light polarization is provided according to another embodiment. The optical element includes at least one waveguide and at least one refractive optical element. The waveguide may be configured to guide light toward the refractive optical element, and the refractive optical element may be configured to deflect light at an angle from the light path within the waveguide. The polarization loss of the light through the waveguide and the refractive optical element may be less than 40% or 20%. The refractive optical element may include two prisms.

Further areas of applicability of the present disclosure will become apparent from the detailed description provided hereinafter. It should be understood that the detailed description and specific examples, while indicating various embodiments, are intended for purposes of illustration only and are not intended to necessarily limit the scope of the disclosure.

Figure 1:
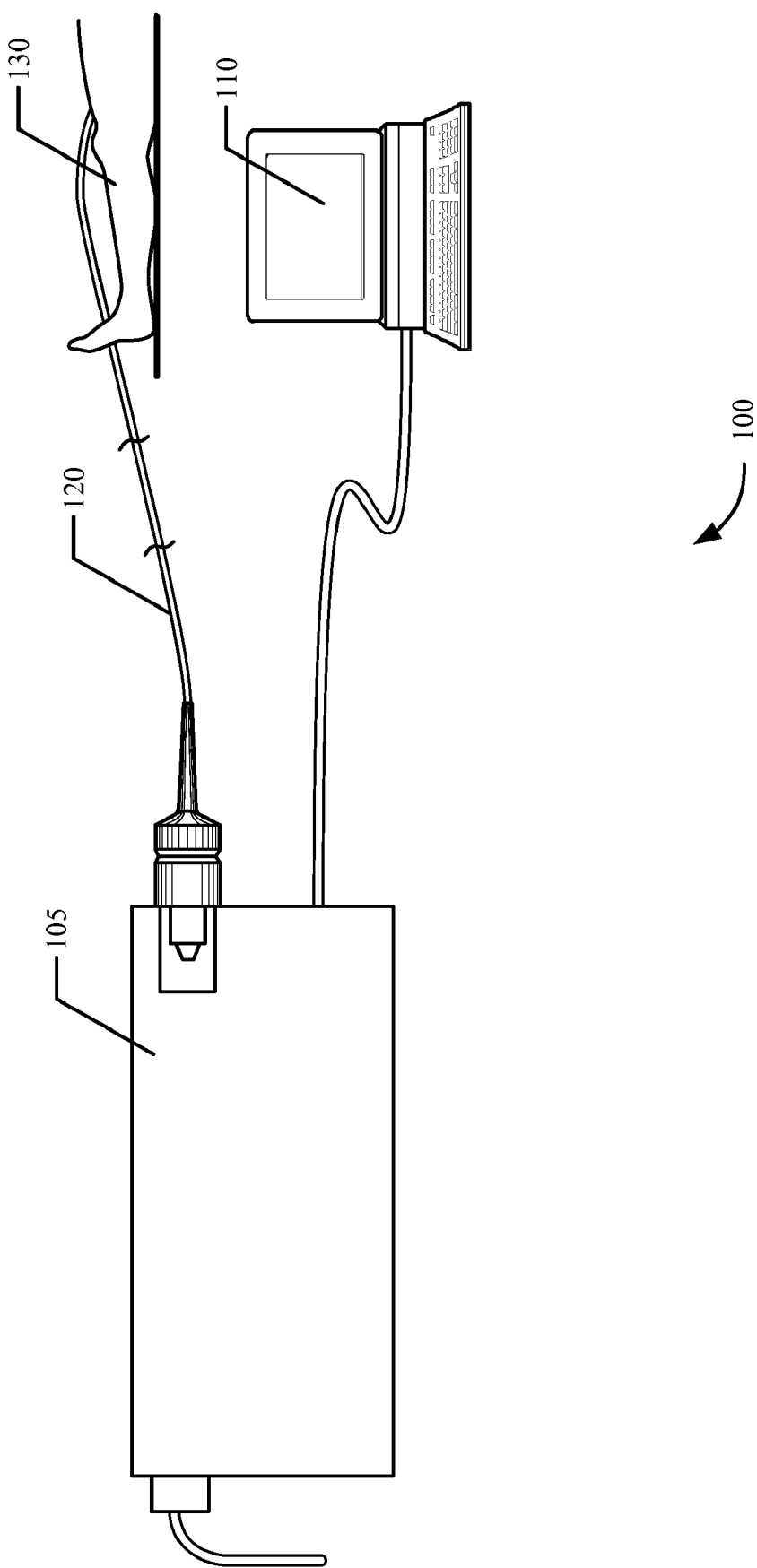
FIG. 1 shows a catheter system according to one embodiment of the invention.

In the appended figures, similar components and/or features may have the same reference label. Where the reference label is used in the specification, the description is applicable to any one of the similar components having the same reference label.

DETAILED DESCRIPTION OF THE INVENTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It being understood that various changes may be made in the function and arrangement of elements without departing from the spirit and scope as set forth in the appended claims.

An optical sensor that provides lateral viewing while maintaining light polarization is provided according to one embodiment of the invention. The sensor may be used, for example, by a physician to monitor nearby tissue while removing a lead from an implanted electrical device such as a lead from a pace maker. Over time an implanted lead may become embedded within the surrounding tissue. Often such leads are removed using a catheter with a hollow inner lumen. The lumen may be placed over the end of the lead and then a cutting device, such as a laser, may be used to ablate any surrounding tissue, free the lead from the tissue, and allow the lumen of the catheter to receive the lead. One cautionary issue with such a procedure is peripheral damage. Knowing the type of tissue and/or the condition of the tissue near the catheter may help the operator know how to use the catheter to remove the electrical lead.

A lateral viewing and polarization maintaining sensor of the embodiments of the present invention may provide images of the tissue surrounding the catheter. Such a catheter may include a light source, a polarizer and a variety of optical elements such as lenses and beam splitters that focus light through a waveguide. The waveguide may direct the light through the sensor body toward an embedded refractive element. The refractive element, for example, may include two equilateral triangle prisms positioned near the distal tip of the catheter such that each prism refracts the light incident thereon approximately 20°-45°. These prisms, in combination, therefore refract the light about 40°-80°. Depending on the prisms selected, the light may be refracted 1° to 179° from the combination of prisms. Refraction is used to direct the light outward from the surface of the catheter because, unlike reflection, refraction losses are relatively polarization independent. The outer body of the sensor may include an aperture from which the light is directed from the refractive element toward a target. Light reflected and/or scattered from the target is returned through the aperture into the refractive elements and back through the waveguide. Various imaging techniques may be used. In one embodiment of the invention PS-OCT algorithms may be used to create PS-OCT images from the light returned from the target. These images may provide a doctor insight into the type of tissue surrounding the lead as the lead is being removed. The information, for example, may be used to change laser operating settings in a laser catheter or may be used to move the catheter further from the tissue.

An optical sensor that provides lateral viewing while maintaining light polarization may be used in any number of applications that require lateral views while maintaining light polarization. For example, the sensor may be used in medical applications such as part of an endoscope or catheter, and in industrial non-destructive applications. Various embodiments of the invention are described below. These embodiments are provided without limitation.

FIG. 1 shows a catheter 100 that provides lateral viewing while maintaining light polarization according to one embodiment of the invention. A source/detector system 105 is shown coupled with a user interface 110. The source/detector system 105 and the user interface, in other embodiments of the invention, may be coupled into one system. The source/detector system 105 is connected with a catheter 120 that may be inserted into a vessel within a human body 130. The catheter 120 is an elongated tube that may include a number of elements. The catheter 120 may be of any suitable length A, with a length A between about 50 cm and about 390 cm. For example, the catheter may be 0.04 inches to 0.16 inches in diameter. The catheter may include at least one optical fiber that transmits light from the source/detector system 105 down at least a portion of the catheter and return reflected light back toward the source/detector system 105. In non catheter embodiments, the sensor body may be of any size and/or dimension.

According to another embodiment of the invention the source/detector system 105 may include a laser and the catheter may include a number of fiber optics. The fiber optics receive light from the laser and conduct the light from the proximal end of the catheter to a target from the distal end of the catheter. The light from the laser may be directed toward a target within a vessel using fiber optics within the catheter. The target may be within various biological vessels, for example, blood vessels, arteries, capillaries, organs, etc. In non medical applications, for example, the vessel may include any type a deep cavity within which non-destructive imaging is required, such as, tubes, chambers, pipes, etc.

Figure 2:
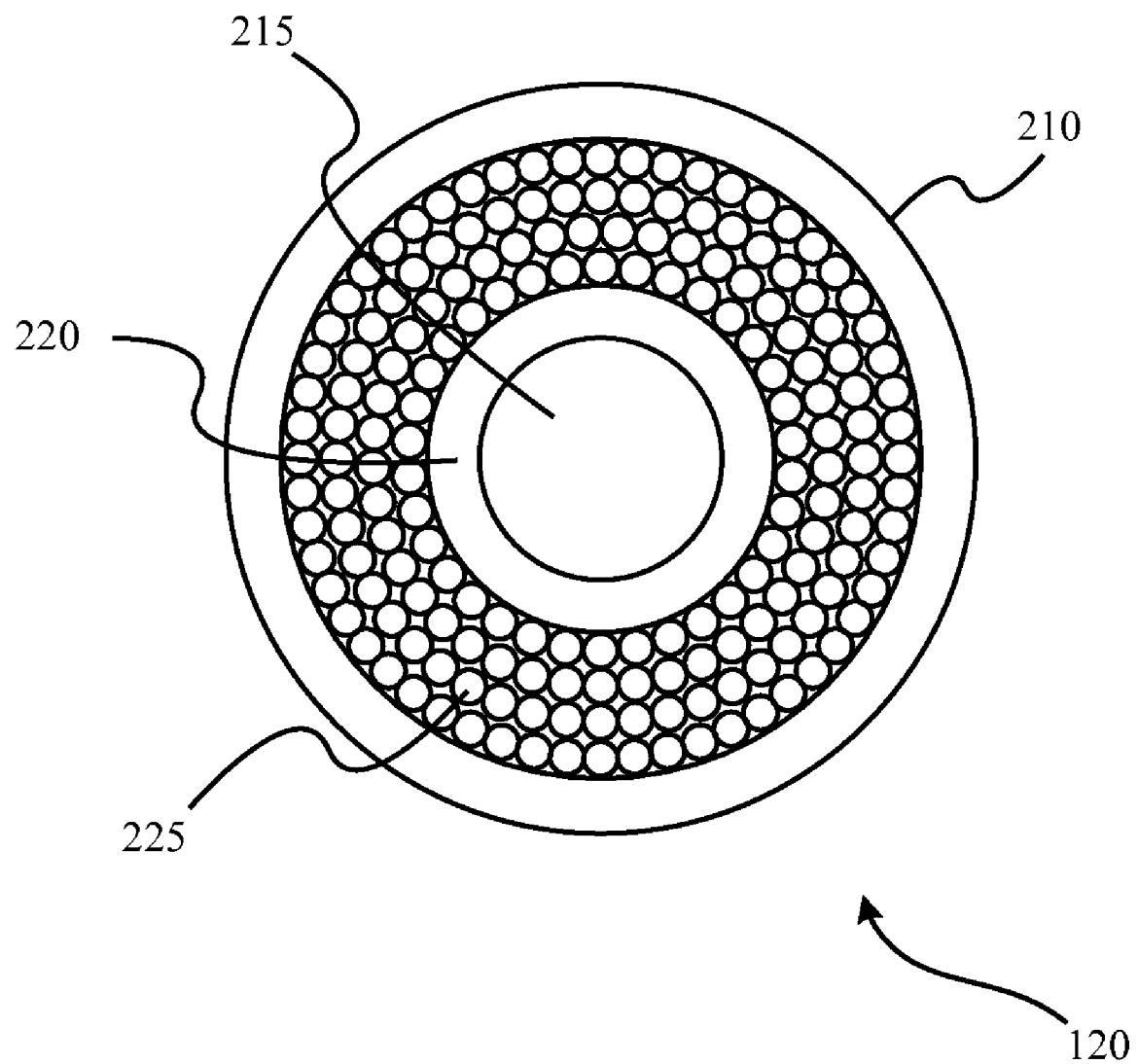
FIG. 2 shows a cross sectional view of a catheter according to one embodiment of the invention.

FIG. 2 shows a cross sectional view of a catheter 120 according to one embodiment of the invention. The catheter 120 includes an outer catheter wall 210 that surrounds a plurality of fiber optics 225. One or more fiber optics may comprise a single mode fiber. Other embodiments may use a polarization-maintaining fiber, a non-polarization maintaining single mode fiber-optic, few-mode or multimode fiber-optic, a solid waveguide and/or a hollow waveguide. One or more fiber optics may include a laterally refractive optical element toward the distal end of the fiber optic. One of the fiber optics may transmit light from a light source through the catheter toward a refractive optical element positioned within the catheter. Moreover, a second laterally refractive element and fiber optic may be placed within the catheter that provides lateral imaging along a longitudinal path of the catheter.

Figure 3:
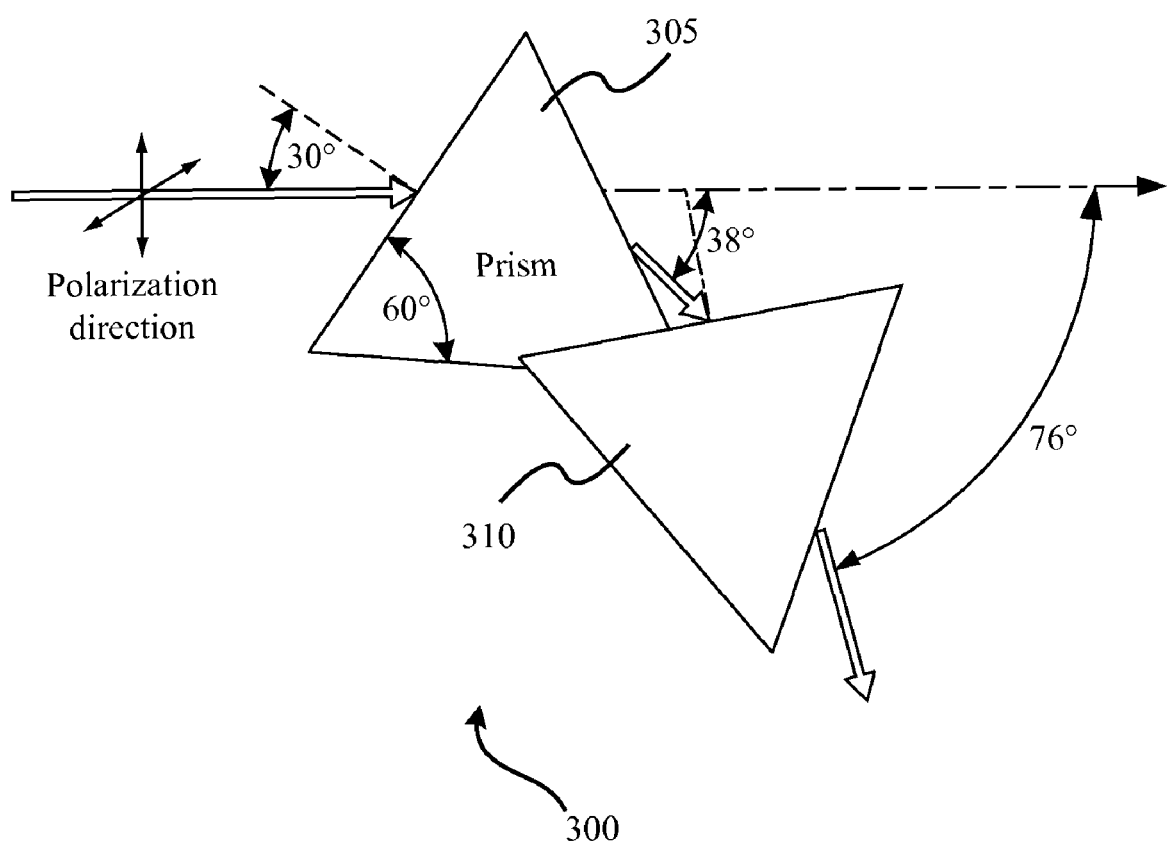
FIG. 3 shows a refractive dual-prism element for a lateral light delivery and detection system according to one embodiment of the invention.

FIG. 3 shows the diagram of a refractive dual-prism element 300 for a lateral light delivery and detection system according to one embodiment. Cross polarized light or elliptically polarized light may be received at a first prism 305. In this embodiment the first prism is an equilateral triangular prism that refracts light 38°. The refracted light from the first prism 305 is then refracted 38° by a second prism 310. Thus the light received at the first prism 305 is refracted a total of 76° by the combination of the two prisms. Additional prisms can be used to increase the angle of deflection. The deflection angle can additionally be manipulated by altering the angle between respective prisms. In contrast the use of single prisms can give a fixed deflection angle. The prism may have more than three corners, or unequal number of corners. Each prism may deflect light different angles. Moreover, more than two prisms may be used.

While two triangular prisms are shown, any type of optical element that refracts light may be used. For example, a non equilateral Triangular prism, an Abbe prism, a Pellin-Broca prism or a Amici prism may be used. Any type of refracting optical element may be used as long as the material is isotropic and, therefore, has a negligible effect on the polarization of the light transmitted through the optical element. For example, materials may be used that loose less than about 50%, 45%, 40%, 35%, 30%, 25%, 20%, 15%, 10%, 5%, 2% or 1% of the polarization of the transmitted light. According to other embodiments of the invention, 1, 2, 3, 4, 5, 6 or more optical elements may be used in conjunction to refract light nearly laterally from the original direction of the light. The light may be refracted through a refractive optical element about 60°, 61°, 62°, 63°, 64°, 65°, 66°, 67°, 68°, 69°, 70°, 71°, 72°, 73°, 74°, 75°, 76°, 77°, 78°, 79°, 80°, 81°, 82°, 83°, 84°, 85°, 86°, 87°, 88°, 89°, or 90° in either direction toward the distal end of the catheter or toward the proximal end of the catheter. In another embodiment of the invention, the light may be refracted from about 0° to 180°.

Refraction through isotropic materials is an ideal way to change the angle of the light transmission without losing the polarization of the light. The polarization effects of reflection depend on the angle of the incident light. Accordingly, during reflection of polarized light, light polarized in one direction is reflected in a different proportion than light polarized in another direction depending on the angle of reflection. Fiber optics may also be bent in order to redirect the light laterally from the catheter, however, a bend large enough to propagate light through the fiber would be greater than the width of a sensor. Thus, due to the limitations in reflection on cross polarized light and in the bend radius of fiber optics, refraction may be used to provide light lateral from the outer catheter surface.

Figure 4:
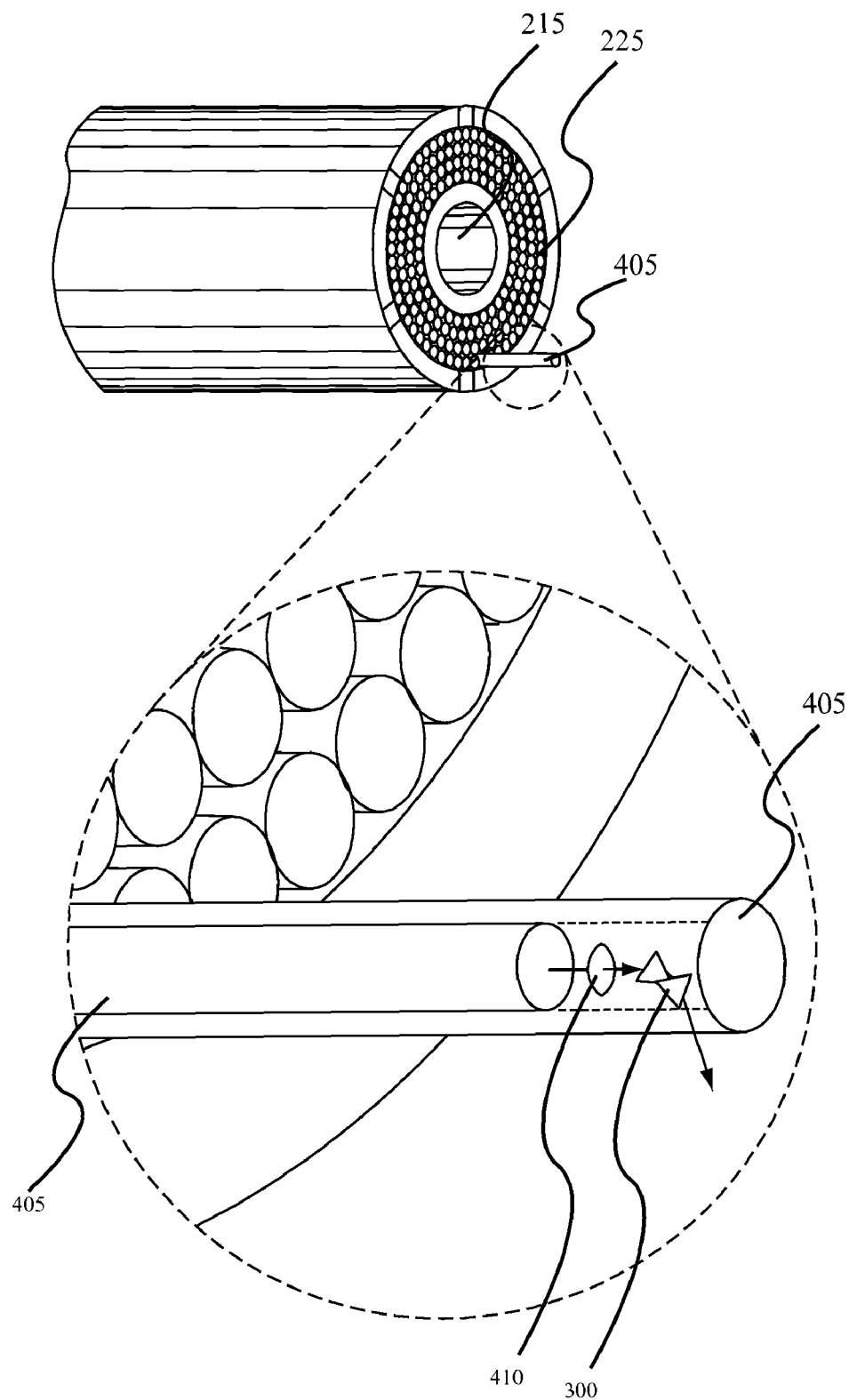
FIG. 4 shows a exploded three-dimensional view of a laser catheter with a lateral light delivery and detection system according to one embodiment of the invention.

FIG. 4 shows a three dimensional view of a laser catheter 120 with a refractive dual-prism 300 element according to another embodiment of the invention. A plurality of fiber optics are shown within a fiber core 225 that run the length of the laser catheter 120. The catheter includes an inner lumen 215. The catheter also includes an outer surface. One or more of the fibers 405 within the fiber core 225, may transmit light from a light source toward the dual prisms 300. A single waveguide 415 including a fiber-optic and prism array, is shown pulled from within the fiber for illustration purposes only. While a dual prism arrangement is shown, any combination of refractive elements or a single refractive element may be used. An optical element, such as a lens 410, may be placed between the end of the fiber 405 and the prisms 300 to focus the light on the first face of the prisms. An optical element, such as a lens (not shown) may be placed between the prisms 300 and the field-of-view (e.g. tissue target) to focus the light. The single waveguide 415, for example, may be a single mode fiber. The outer surface 310 of the catheter may include a aperture (not shown) from which light refracted by the prisms may exit and/or enter the catheter. The prisms 300 may both refract light from the fiber 405 toward a target as well as refract light reflected from the surface of the target back through the fiber 405.

The prisms, for example, may comprise glass, fused silica, sapphire, plastic or quartz. The prisms, for example, may be between 50 and 100 micrometers, but not limited to these dimensions.

Figure 5:
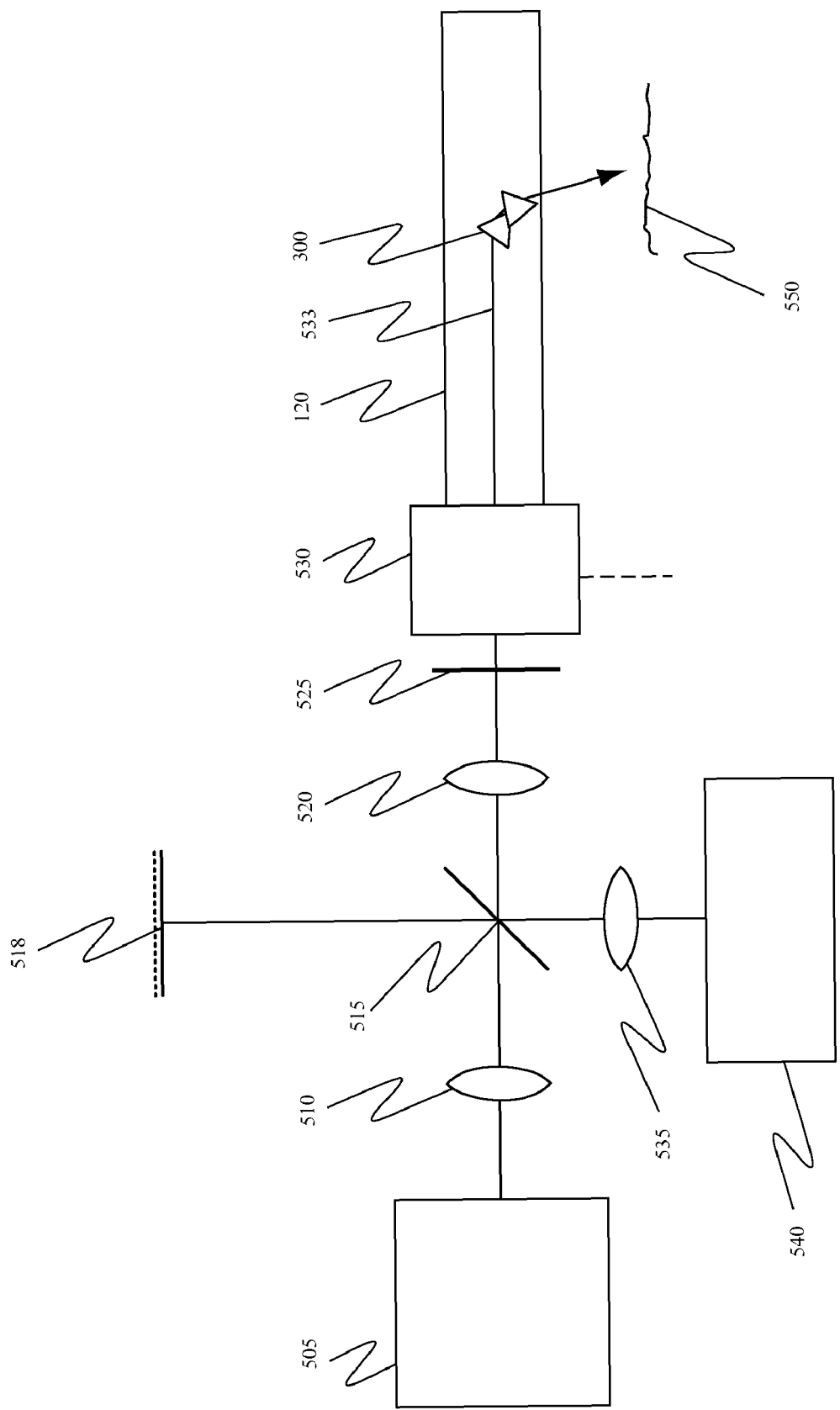
FIG. 5 shows a block diagram of polarization sensitive optical coherence tomography system according to one embodiment of the invention.

FIG. 5 shows a block diagram of a PS-OCT system according to one embodiment of the invention. OCT uses low-coherence interferometry to provide micrometer tissue imaging resolution. In this example, a catheter 120 is shown with light source 505, a beam splitter 515, a mirror 518, a fiber 533, lenses 510, 520, 535 and a refracting optical element 300, which, as shown, includes two prisms. The light source may include a laser, LED(s), and/or superluminescent diodes. The light from the light source may include a single source with a single center wavelength or multi-band with multiple center wavelengths. A detector 540 is also shown along with various other optical elements. The detector 540 may include, but not limited to, a CCD, one dimensional array, two dimensional array, polarization devices or the like. A polarizer unit 525, which may include more than 1 component, as known to anyone skilled in the art, may be included to polarize the light from the light source. The polarizer, for example, may cross polarize the light or elliptically polarize the light. An optional coupler 530 positioned at the proximal end of the catheter device 120, may rotate or translate the incident beam of light to perform cross-sectional or longitudinal imaging of the vessel optical properties.

The detector 540 may be a photosensitive detector, such as a photosensitive diode or other device. The detector may also include appropriate signal amplifying and/or measuring circuitry, for example, such as are used in conventional optical coherence tomography devices, to provide signals representative of detection by the photosensitive detector. The detector 540 may also include a signal processing circuit or module, such as an electronic circuit, a lock-in amplifier and/or a computer. The detector may include two detectors, each of which detects light at different polarizations. The detector may detect light incident from the surface of a target in different polarizations. The computer may be coupled with the detector to carry out various data storage and data processing functions on the detected images.

The beam splitter 515 may be a 50/50 beam splitter or some other ratio splitter. The beam splitter creates an interferometer. An interferometer uses the superimposition (interference) of two or more waves, to detect miniscule differences between them. The interferometer relies on the interference of two paths with identical length to recombine to provide the exact similar conditions in wave length path length, only this pattern is distorted in one of the paths due to the presence of a dispersive target medium (tissue or other). The beam splitter permits light to travel along two optical arms: toward the detector (reference arm) and through the catheter toward a target (sample arm). The path length of the two arms may be adjusted to provide approximately equal path lengths. The combination of reflected light from the sample arm and reference light from the reference arm gives rise to an interference pattern. Areas of the sample that reflect back a lot of light will create greater interference than areas that don't. Any light that is outside the short coherence length will not interfere. This reflectivity profile, may contain information about the spatial dimensions and location of structures within the item of interest. A cross-sectional tomograph may be achieved by laterally combining a series of these axial depth scans.

The detector and/or computer may provide unbalanced cross polarized scans to a display. Cross polarized scans may be combined to produce a cross polarized image known to anyone skilled in the art. Circular polarization may also be used. Such an image may be used by a doctor to determine tissue type and consistency near the catheter. For instance, muscle tissue imaged under cross polarization may provide a differently organized image than the collagen in bones, tendons, plaque as well as vessel wall and cartilage in addition to smooth muscle and cardiac muscle as well as neural tissues. Moreover, such images may provide a visual representation of the relative distance between the catheter and any material near the outer surface of the catheter.

The PS-OCT system uses two optical arms to provide interference at the detector. In the first arm, light travels from the light source 505, is reflected from the beam splitter 515, toward the mirror 518, and is reflected back toward the detector 540. As shown, light may also pass through one or more number of optical elements in the first arm, such as, for example, a lens, a filter, a polarizer, etc. In the second arm, light travels from the light source 520, is transmitted through the beam splitter 515 into the fiber 533, is deflected laterally by the prisms 300 and is incident on the target 550. The light is reflected/scattered by the target 550 back through the prisms 300, through the fiber optic 533, and is reflected at the beam splitter 515 toward the detector 540. In one embodiment the mirror 518 may be manually or automatically adjusted in order to provide the proper path length for interference at the detector.

Figure 6:
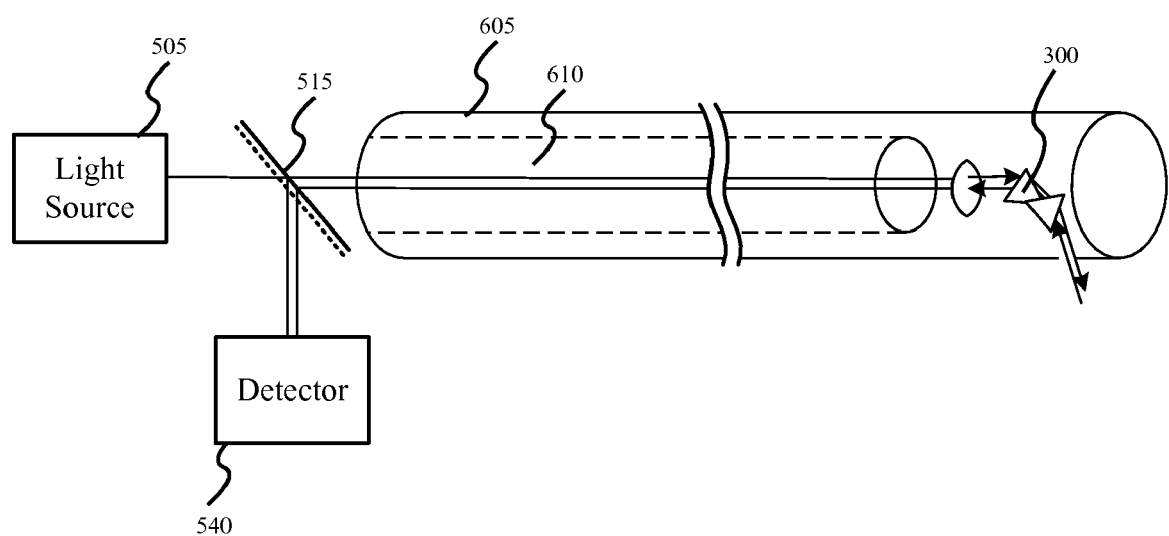
FIG. 6 shows an optical sensor that provides lateral viewing while maintaining light polarization according to one embodiment of the invention.

FIG. 6 shows an optical sensor that provides lateral viewing while maintaining light polarization according to one embodiment of the invention. The sensor includes a sensor body 605 comprising a proximal end and a distal end. Coupled with the sensor body is a light source 505, a beam splitter 515, and a detector 540. The light source produces light that is transmitted to the beam splitter. The light source may include a laser, LED(s), and/or superluminescent diodes. The light from the light source may include a single source with a single center wavelength or multi-band with multiple center wavelengths. The light source may also produce polarized light, such as cross polarized or elliptically polarized light. The detector 540 may include, but not limited to, a CCD, one dimensional array, two dimensional array, polarization devices or the like.

At the beam splitter a portion of the light is transmitted to the detector 540 and another portion is transmitted through a waveguide 610 that is within the sensor body 605. The waveguide 610 guides the light through the sensor body toward the refractive optical element. In this case the refractive optical element includes two prisms 300. The light is deflected laterally from the axial path within the sensor through an aperture in the sensor body toward a target. Light scattered from the target is refracted back through the two prisms and directed down the waveguide where it is reflected toward the detector 540.

While some embodiments of the invention have been described with reference to a PS-OCT catheter system for use within a human vessel, embodiments of the invention are not limited thereto. For instance, embodiments of the invention may be used in RF-ablation catheters and balloon catheters. Embodiments of the invention may be used for stent placement as well. Additionally, embodiments of the invention may be used in an endoscope applications. Embodiments of the invention may also be used in non medical applications such as non-destructive testing of cavities and vessels.

Specific details are given in the above description to provide a thorough understanding of the embodiments. However, it is understood that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Implementation of the techniques, blocks, steps and means described above may be done in various ways. For example, these techniques, blocks, steps and means may be implemented in hardware, software, or a combination thereof. For a hardware implementation, the processing units may be implemented within one or more application specific integrated circuits (ASICs), digital signal processors (DSPs), digital signal processing devices (DSPDs), programmable logic devices (PLDs), field programmable gate arrays (FPGAs), processors, controllers, micro-controllers, microprocessors, other electronic units designed to perform the functions described above and/or a combination thereof.

Also, it is noted that the embodiments may be described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be rearranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, scripting languages, firmware, middleware, microcode, hardware description languages and/or any combination thereof. When implemented in software, firmware, middleware, scripting language and/or microcode, the program code or code segments to perform the necessary tasks may be stored in a machine readable medium, such as a storage medium. A code segment or machine-executable instruction may represent a procedure, a function, a subprogram, a program, a routine, a subroutine, a module, a software package, a script, a class, or any combination of instructions, data structures and/or program statements. A code segment may be coupled to another code segment or a hardware circuit by passing and/or receiving information, data, arguments, parameters and/or memory contents. Information, arguments, parameters, data, etc. may be passed, forwarded, or transmitted via any suitable means including memory sharing, message passing, token passing, network transmission, etc.

For a firmware and/or software implementation, the methodologies may be implemented with modules (e.g., procedures, functions, and so on) that perform the functions described herein. Any machine-readable medium tangibly embodying instructions may be used in implementing the methodologies described herein. For example, software codes may be stored in a memory. Memory may be implemented within the processor or external to the processor. As used herein the term "memory" refers to any type of long term, short term, volatile, nonvolatile, or other storage medium and is not to be limited to any particular type of memory or number of memories, or type of media upon which memory is stored.

Moreover, as disclosed herein, the term "storage medium" may represent one or more devices for storing data, including read only memory (ROM), random access memory (RAM), magnetic RAM, core memory, magnetic disk storage mediums, optical storage mediums, flash memory devices and/or other machine readable mediums for storing information. The term "machine-readable medium" includes, but is not limited to portable or fixed storage devices, optical storage devices, wireless channels and/or various other mediums capable of storing, containing or carrying instruction(s) and/or data.

While the principles of the disclosure have been described above in connection with specific apparatuses and methods, it is to be clearly understood that this description is made only by way of example and not as limitation on the scope of the disclosure.

What is claimed is:

1. An optical sensor that provides lateral viewing while maintaining light polarization, the sensor comprising:
    an endovascular catheter comprising a proximal end and a distal end;
    at least one waveguide including a distal end and a proximal end, wherein the proximal end of the waveguide is coincident near the proximal end of the endovascular catheter, the distal end of the waveguide is coincident at a point near the distal end of the endovascular catheter, and the waveguide is positioned within the endovascular catheter; and
    at least one refractive optical element positioned within the endovascular catheter near the distal end of the waveguide, wherein the refractive optical element is configured to refract light received from the distal end of the waveguide laterally from the endovascular catheter while maintaining the polarization state of the light, and wherein the at least one refractive optical element and the waveguide are configured such that the polarization state of light loses less than 40% of the light's polarization.

2. The sensor according to claim 1, wherein the waveguide comprises a fiber optic.

3. The sensor according to claim 1, wherein the refractive optical element comprises one or more multi angular prism.

4. The sensor according to claim 1, wherein the refractive optical element comprises two prisms.

5. The sensor according to claim 4, wherein the at least two prisms comprise a first prism and a second prism, the first prism is configured to receive light from the waveguide and refract the light at an angle of about 20° to about 45° measured from the outer surface of the endovascular catheter, and the second prism is configured to receive light from the first prism and refract the light at an angle of about 20° to about 45° measured from the outer surface of the endovascular catheter.

6. The sensor according to claim 4, wherein the at least two prisms are coupled as a single element.

7. The sensor according to claim 1, wherein the waveguide comprises a single mode fiber optic.

8. The sensor according to claim 1, wherein the refractive optical element refracts light at an angle of about 40° to about 90° measured from the outer surface of the endovascular catheter.

9. The sensor according to claim 1, further comprising a lumen within the endovascular catheter and an opening at the distal end of the sensor coupled with the lumen.

10. The sensor according to claim 1, further comprising a beam splitter coupled with the proximal end of the waveguide, one or more light sources coupled with the beam splitter, and a detector coupled with the beam splitter, wherein the light source produces light that is propagated through the beam splitter and waveguide, and refracted by the refractive optical element toward a target, and wherein the refractive optical element refracts light reflected from the target through the refractive optical element through the waveguide and toward the detector through the beam splitter.

11. The sensor according to claim 10, wherein the light source produces at least one of cross-polarized light and elliptically polarized light.

12. The sensor according to claim 1, wherein the endovascular catheter includes an aperture configured to allow light refracted from the refractive optical element to pass through the endovascular catheter toward a target and configured to allow light reflected from the target to pass through the endovascular catheter toward the refractive optical element.

13. A method for using an endovascular catheter that provides lateral viewing while maintaining light polarization, the method comprising:
    inserting the endovascular catheter into a target of interest;
    conducting light from a light source through a waveguide within the sensor toward the distal end of the sensor;
    refracting light laterally from the sensor toward the target using a refractive optical element;
    refracting light scattered from the target using the refractive optical element within the sensor and conducing the light scattered from the sensor toward the proximal end of the sensor through the waveguide, wherein the refractive optical element is configured to lose less than about 40% of the polarization of refracted light polarization of the light is maintained during refraction by the refractive optical element.

14. The method according to claim 13, wherein the light is refracted an angle greater 50° and less than or equal to 90° from the longitudinal direction of the sensor.

15. The method according to claim 13, further comprising receiving the light scattered from the target at a light detector.

16. The method according to claim 13, wherein the refractive optical element comprises one or more prisms.

17. The method according to claim 13, wherein light passes through a beam splitter after leaving the light source and prior to entering the waveguide.

18. The method according to claim 13, wherein light passes through a beam splitter after leaving the waveguide and prior to being received at a light detector.

19. The method according to claim 13, wherein the light detector detects light in more than one polarization state.

20. The method according to claim 13, further comprising providing an image of the target using PS-OCT algorithms from the light received at the detector.

21. A catheter that provides lateral viewing while maintaining light polarization, the catheter comprising:
    a catheter body configured to be inserted into a vessel within a human body;
    a light source is configured to provide cross-polarized light and is coupled with the catheter body;
    at least one fiber optic including a distal end and proximal end, wherein the proximal end of the fiber optic is coincident near the proximal end of the catheter body, the distal end of the fiber optic is coincident at a point near the distal end of the catheter body, the fiber optic is positioned within the catheter body, and the fiber optic receives light from the light source at the proximal end of the fiber optic and guides the light to the distal end of the fiber optic; and
    at least two prisms positioned within the catheter near the distal end of the fiber optic, wherein the at least two prisms are configured to refract light received from the distal end of the fiber optic outward from the catheter, wherein the at least two prisms are configured such that the polarization state of light loses less than about 40% of polarization of refracted light.

22. An optical element that provides lateral viewing while maintaining light polarization comprising at least one waveguide coupled with at least two prisms, wherein the waveguide is configured to guide light toward the at least two prisms, the at least two prisms is configured to deflect light at an angle from the light path within the waveguide, and the polarization loss of the light through the waveguide and the at least two prisms are less than 40%.

23. The optical element according to claim 22, wherein the at least two prisms comprises three or more prisms.

24. The optical element according to claim 22, wherein the polarization loss of the light through the waveguide and at least two prisms is less than 20%.

25. The optical element according to claim 22, wherein the at least two prisms comprises a first equilateral triangle prism and a second equilateral triangle prism.

26. The optical element according to claim 22, wherein each of the at least two prisms is configured to refract light incident thereon at an angle of about 20° to about 45° degrees measured from an outer surface of the catheter body.

* * * * *